United States Patent [19]
Fisher

[11] Patent Number: 5,501,697
[45] Date of Patent: Mar. 26, 1996

[54] TREATMENT DEVICE TO AID IN LONG-TERM CESSATION OF SMOKING

[76] Inventor: Gary R. Fisher, 2251 Federal Ave., Los Angeles, Calif. 90064

[21] Appl. No.: 902,970

[22] Filed: Jun. 23, 1992

[51] Int. Cl.⁶ .................................................. A61B 17/00
[52] U.S. Cl. .................................................. 606/204
[58] Field of Search ................................. 606/201–204, 606/189

[56] References Cited

U.S. PATENT DOCUMENTS

| | | | |
|---|---|---|---|
| 4,308,861 | 1/1982 | Kelly | 606/204 |
| 4,384,583 | 5/1983 | Speelman et al. | 606/203 |
| 4,479,495 | 10/1984 | Isaacson | 606/204 |
| 4,590,939 | 5/1986 | Sakowski | 606/204 |
| 5,078,728 | 1/1992 | Giarratano | 606/201 |

*Primary Examiner*—Stephen C. Pellegrino
*Assistant Examiner*—William W. Lewis
*Attorney, Agent, or Firm*—Henry M. Bissell

[57] ABSTRACT

A removeably attachable wrist band device for use in helping an addicted cigarette smoker permanently quit smoking. The device comprises an elastic section, a hook fastener section, a loop fastener section, and an acupressure stimulator. The device is placed on a user's wrist such that the acupressure stimulator is positioned proximal to the L-7 acupuncture point and the elastic section of the wrist band is positioned on top of the user's wrist. The elastic section of the wrist band is designed to limit the maximal energy that the user can transfer to a unit area of skin when the band is snapped against the wrist. This is so that snapping the wrist band will not be perceived as aversive to the user. The disclosed wrist band has the dual functions of providing a non-aversive behavioral modification device together with providing continuous and differential stimulation of the L-7 acupuncture point, which has therapeutic value in treatment of smoking addiction.

26 Claims, 1 Drawing Sheet

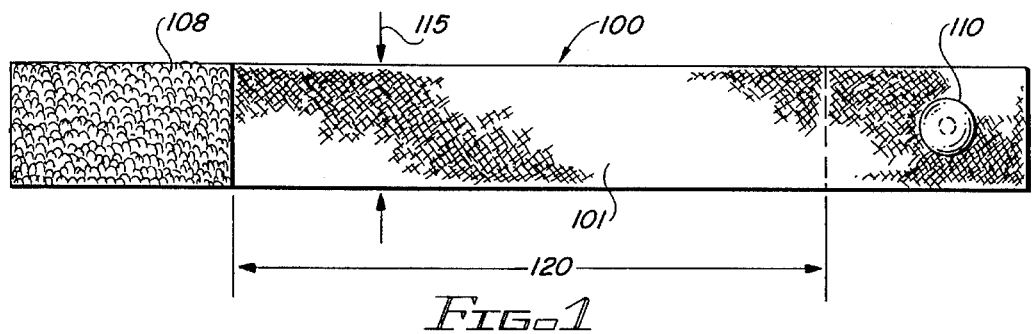
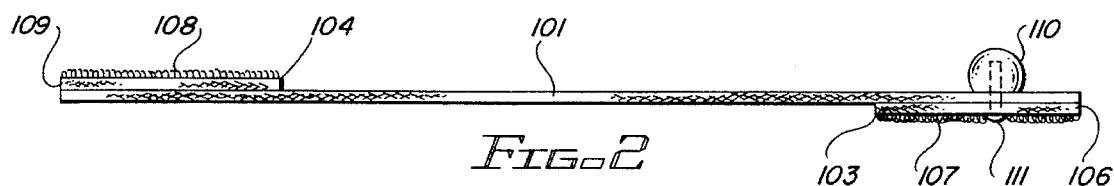
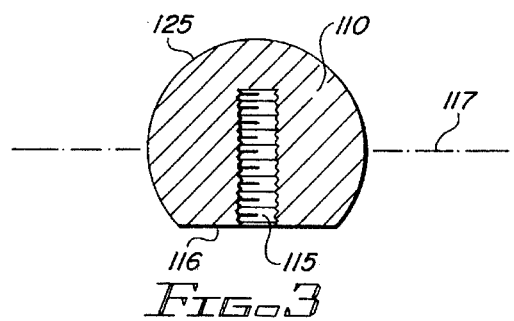
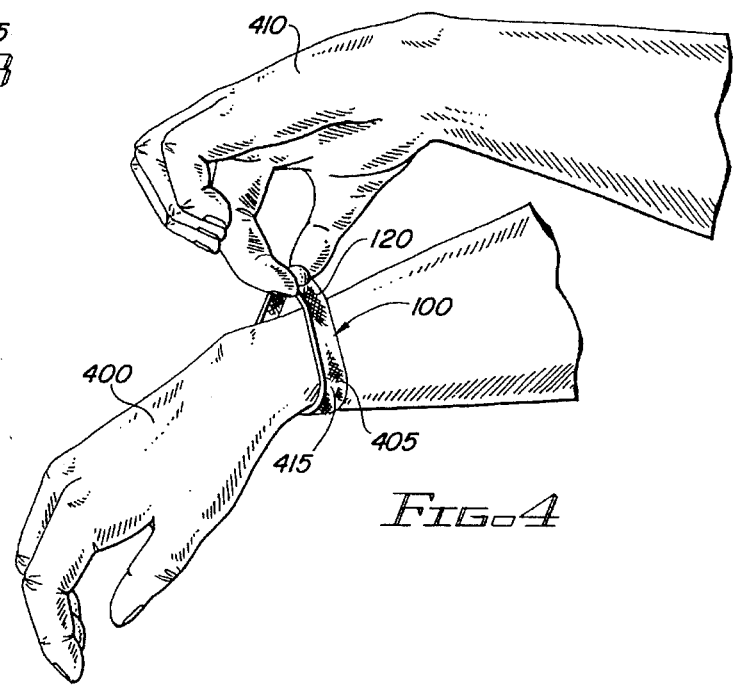

TREATMENT DEVICE TO AID IN LONG-TERM CESSATION OF SMOKING

BACKGROUND OF THE INVENTION

1. Field of the Invention

This invention relates to the fields of psychology and acupuncture and specifically to a device to aid a person in quitting cigarette smoking.

2. Discussion of Related Art

Cigarette smoking is a particularly tenacious addiction. As contrasted to use of illegal drugs, smoking is tolerated in a variety of every day situations. Thus the smoker has the unfortunate opportunity to integrate cigarette usage into virtually every aspect of his daily life.

The addicted smoker develops strong psychological dependencies and habit patterns that remain for many months after nicotine is eliminated from the body. Therefore, quitting smoking is considerably more difficult than simply ridding the body of nicotine.

The physical dependency to nicotine has a strong psychopharmacological basis. Yet surprisingly, nicotine has a half life of just two hours and its principal metabolite, cotinine, has a half life of three to nineteen hours [see Benowitz, N. (1983) "The Use of Biologic Fluid Samples in Assessing Tobacco Smoke Consumption" in NIDA Research Monograph #48; U.S. Department of Health and Human Services. pp. 6–26]. In general, 24 to 48 hours are required for nicotine to be completely eliminated from the body and approximately two weeks for metabolic and other components to be eliminated. Thus, a treatment adjunct that can and will be used for long periods of time after physical addiction is quelled is highly desirable.

Most researchers in the field report that the highest success rates for quitting smoking involve the use of a number of treatment modalities. With the exception of dying from cigarette smoking related causes, there is no sure-fire single method of quitting smoking.

Pharmacological adjuncts have been employed to treat the physical addiction to nicotine. Among these, nicotine polacrilex (gum) has been used in several clinical and self-management programs. In terms of the gum's efficacy, Brown and Emmons (1991) report that "it may be more effective in increasing short-term abstinence, rather than long term outcome." [Brown, R. A. and K. M. Emmons (1991). "Behavioral Treatment of Cigarette Dependence" in *The Clinical Management of Nicotine Dependence.* J. A. Cocores, ed.; Springer-Verlag. New York. p.110]. The current interest in the nicotine "patch" may very well carry the same limitation regarding its long term efficacy.

A review of a variety of aversion therapy techniques is given by Smith (1991) [in *The Clinical Management of Nicotine Dependence.* J. A. Cocores, ed.; Springer-Verlag. New York pp. 135–149]. Among short term techniques that have been used are focused smoking, rapid smoking, taste aversion, faradic (electric) shock, and covert sensitization. In general, these techniques have been employed during and immediately after the period in which the smoker is still physically addicted to nicotine and, with the possible exception of covert sensitization, are not appropriate for use on a long-term basis.

Faradic shock has been employed in a number of clinical treatments and is a part of the short-term treatment paradigm used by the Schick Center.

Symmes, [U.S. Pat. No. 3,885,576], disclosed a device comprising a wrist band with a mercury switch that induces an electric shock when the user raises his hand to (ostensibly) bring a cigarette to his lips. This and other conceptually similar devices have an inherent drawback when used to curb cigarette addiction. For example, Powell and Azrin (1968) in a study of self-administered electric shock to limit cigarette intake, found that the greater the shock intensity the less time the subjects tended to use the device [Powell, J. R. and N. Azrin. (1968) *Appl. Behav. Anal.* Vol 1, p.63–71]. The authors concluded that the subjects developed an aversion to the shock technique itself, which would suggest a limitation to its long term utility. In other words, it is doubtful that users would employ such a device on a self-administered basis after the physical dependency stage of cigarette addiction is over.

Use of a wrist-worn rubber band has been suggested by Glynn and Manley (1976) as one of a number of behavioral-modification techniques to aid smokers in quitting [Glynn, T. and M. Manley. (1976) *National Cancer Institute Manual For Physicians.* U.S. Dept. of Health and Human Services. p.46]. The authors suggest that the band be snapped each time the smoker wants a cigarette and be accompanied by the smoker imagining a stop sign and repeating the word "stop" in his mind.

The foremost drawback of a wrist-worn rubber band for curbing cigarette addiction is that a rubber band is highly extensible and therefore the user can self-inflict considerable pain and erythema depending upon how aggressively he "snaps" the band. As the research of Powell and Azrin suggests, the user may very likely develop an aversion to the rubber band's "sting" and cease its use. On the other hand a wrist band especially designed to limit the maximum "sting" to an acceptably low level may very well enhance the "snap" technique's efficacy for long-term behavior modification due to its acting as an associative agent rather than an aversive therapy device.

Another drawback to the use of a wrist-worn rubber band as described above is that the rubber band has low face validity to the user as a treatment device. The very fact that the band has ubiquitous uses and is essentially cost-free may lower its perceived potential effectiveness in the user's mind.

A third drawback of the wrist-worn rubber band is that it is not adjustable.

Acupuncture has been used to treat a variety of drug dependencies including cigarette addiction. For treatment of nicotine addiction, Kutchins (1991) prescribes stimulation of the L-7 (Lieque) acupuncture point (proximal to the wrist crease) and lung points of the ear [Kutchins, S. (1991) "The Treatment of Smoking and Nicotine Addiction with Acupuncture" in *The Clinical Management of Nicotine Dependence.* J. A. Cocores, ed.; Springer-Verlag. New York pp. 169–180]. He reports that in some cases stimulation of L-7 alone is sufficient in that stimulation of the lung points of the ear tend to replicate L-7 in treatment of the addiction. As with more traditional approaches, Kutchins recommends acupuncture be a part of a multi-faceted approach to treatment. Kutchins reports that use of acupuncture is efficacious and supported by clinical evidence—especially in the short term context.

Isaacson [U.S. Pat. No. 4,479,495] discloses an acupressure point stimulator mounted to an adjustable strap for use in stimulating acupuncture points on the limbs. In use, an appropriate stimulator is positioned over the desired acupuncture point and the strap tightened so as to exert force on the region of the desired point. When used on a lower extremity, limb movement (for instance, walking) provides differential stimulation to the chosen point. However, if the device is used on the lower arm, no such differential stimulation will occur during normal arm movement. Due to adaptation effects, this would limit the effectiveness of Isaacson's device when worn on the arm for long periods.

What is needed is a device which is simple and economical to fabricate and to use, is not subject to the disadvantages mentioned hereinabove with respect to the prior art approaches to solving the problem, and which is effective as an aid to breaking the smoking habit. The present invention combines the treatment modalities of a "snappable" wrist band with limited "sting potential" and an L-7 acupuncture point stimulator. This treatment combination is advantageously made possible by the proximity of acupuncture point L-7 to the wrist crease.

SUMMARY OF THE INVENTION

The invention provides a removeably attachable wrist band for use in helping an addicted cigarette smoker permanently quit smoking.

The wrist band of the present invention is adjustable so that it can fit a wide range of wrist circumferences. Hook and loop fasteners are employed for securing the band around the wrist. Advantageously, the hook and loop fasteners resist the shear force generated when the wrist band is stretched prior to release.

The elastic portion of the band is designed to limit the band's "sting potential" thus taking the device out of the realm of classical aversion therapy and further reducing the likelihood of users developing an aversion to the wrist band for long term use.

The present invention also allows continuous stimulation of the L-7 acupuncture point together with differential stimulation of L-7 when the elastic portion of the band is stretched or when the band is pressed in the region of the stimulator.

Snapping the band acts as an on-going associative technique for the smoker to become consciously aware of the context in which he desires each cigarette. This helps the smoker confront the pervasiveness of the habituation and psychological dimensions of his addiction. Further, by forming a mental image of being "smoke-free" each time the band is snapped and the desire to smoke arises, the smoker re-enforces his decision to quit.

Importantly, the band of the present invention can be worn and used for many months after physical addiction is quelled providing both behavioral modification benefits and continuous and differential stimulation to acupuncture point L-7, which in combination reduce the possibility of recidivism.

In the preferred embodiment of the invention, the wrist band comprises an elastic section, a hook fastener section, a loop fastener section, and an L-7 acupressure stimulator operatively attached to the loop fastener section of the wrist band.

The wrist band is made adjustable by use of hook and loop fasteners which advantageously resist the shear force generated when the band is used according to the invention.

The wrist band is attached to the user's wrist such that the acupressure stimulator is positioned proximal to the L-7 acupuncture point and the elastic section of the wrist band is positioned on top of the user's wrist. The maximal energy transferable by the wrist band to a unit area of skin, when the band is stretched and released, is controlled by both the width of the wrist band and its elastic composition. By constraining this maximal energy to a level wherein the maximum "sting" the user can self-inflict is non-aversive, the user is prevented from developing an aversion to the wrist band.

Snapping the wrist band has the dual functions of providing the user with associative techniques for confronting the habit and psychological components of his addiction, and providing continuous and differential stimulation of the L-7 acupressure point, which has therapeutic value in treatment of smoking addiction.

BRIEF DESCRIPTION OF DRAWINGS

A better understanding of the present invention may be realized from a consideration of the following detailed description, taken in conjunction with the accompanying drawings in which:

FIG. 1 is a top view of the wrist band portion of arrangements in accordance with the present invention;

FIG. 2 is a side view of the wrist band of FIG. 1;

FIG. 3 is a side sectional view of an acupressure stimulator element of arrangements in accordance with the present invention; and FIG. 4 is a perspective view of the wrist band shown in place on a user's right wrist region with the stimulator element positioned over acupuncture point L-7 and illustrating the band in stretched position prior to release.

DESCRIPTION OF THE PREFERRED EMBODIMENT

While the male personal pronoun is employed in the description to follow, it should be understood that the device disclosed herein is intended for both males and females.

FIGS. 1 and 2 are top and side views, respectively, of wrist band 100. The wrist band comprises elastic section 101, loop fastener section 103, hook fastener section 104, and acupressure stimulator 110.

Loop fastener section 103 is comprised of a plurality of loops 107 operatively attached to a flexible non-elastic backing 106. Backing 106 is attached to elastic section 101 as shown in FIGS. 1–2. Backing 106 can be physically attached by adhesive, stitching or equivalent means.

Hook fastener section 104 is comprised of a plurality of plastic hooks 108 operatively attached to flexible non-elastic backing 109. Backing 109 is attached to elastic section 101 at location 109 by adhesive, stitching or equivalent means. Hook and loop fastener sections 103, 104 are adapted to mutually engage each other on contact and are preferably Velcro (™).

By reference to FIG. 2, hook section 104 and loop section 103 are shown attached on opposite ends and on opposing sides of elastic section 101. The purpose of this orientation is to allow wrist band 100 to be removeably attachable to a human wrist. Advantageously, the hook and loop fastener sections allow wrist band 100 to fit a broad range of wrist sizes. Additionally, hooks 108 and loops 107, when engaged, effectively resist the shear force generated by stretching elastic section 120 (FIG. 1) when wrist band 100 is used as intended with this invention.

Elastic section 101 is comprised of an elastic fabric preferably of braided polyester and rubber. Since hook fastener section 104 and loop fastener section 103 are intimately attached to elastic section 101, only section 120 of the wrist band in FIG. 1 is capable of extensibility.

In order to limit the maximum "sting potential" of the wrist band to a level below which it will be perceived as aversive, the maximal energy that can be transferred by "snapping" the band to a unit area of skin must be limited. This requires that the maximum elongation of the wrist band, its width, and the force required to attain maximum elongation be determined on an empirical basis.

To meet this requirement a number of elastic fabrics were tested. It was found that polyester/rubber braided fabrics with a maximum elongation of 100%, a width between 0.5 inches and 1.0 inches, and a tensile force of five pounds to attain maximum elongation were conservatively perceived to be non-aversive. Further, with these values no erythema was observed after repeated "snaps".

Since the inventor has an average threshold of pain and since pain thresholds vary with different individuals, the above values were intentionally chosen to be in the less-aversive rather than more-aversive region.

One suitable elastic fabric meeting the above criteria is manufactured by Rhode Island Textile Company [Stretchrite Elastic (®) #SS34.] This is a ¾" wide longitudinally braided fabric containing 69% polyester and 31% rubber.

FIG. 2 shows acupressure stimulator 110 attached to elastic section 101 by means of screw 111.

The purpose of stimulator 110 is to stimulate acupuncture point L-7 when wrist band 100 is wrapped around the user's wrist with 110 in contact with the skin surface immediately over the L-7 acupuncture point. The location of L-7 is described in *Acupuncture—A Comprehensive Text*, [Eastland Press, Chicago; J. O'Connor & D. Bensky, trans. (1981) p.243–244] as being proximal to the styloid process of the radius, above the wrist crease in a small hollow and anatomically between the tendons of the brachioradialis and the abductor pollicis longus muscles. The drawing on page 244 of the text illustrates how the opposing hand can be employed to easily locate the hollow. Advantageously, differential stimulation of L-7 arises each time the band is stretched or when the user presses the wrist band proximal to stimulator 110.

A side sectional view of stimulator 110 is shown in FIG. 3. Recess 115 is tapped to receive screw 111. As shown in FIG. 2, elastic section 101 and loop fastener section 103 are bored to receive screw 111. This allows choice of different stimulators to be removeably applied to wrist band 100 depending, for instance, on the anatomical and osteological development of a particular user and on the length of time from smoking cessation. Although not shown in FIG. 3, recess 115 could alternatively be bored to receive a press-fit rivet. This would be indicated if a single non-removable acupressure stimulator were to be used during the entire treatment period.

The surface of stimulator 110 is described at least partially by a generally curved surface 125 and a generally flat truncation surface 116 for mating with wrist band 100. For illustrative purposes, the shape shown for the stimulator in FIG. 3 is a truncated sphere although ellipsoidal, parabolic, or other mathematical forms could alternatively be specified.

In FIG. 3 the truncated sphere is illustrated with truncation plane 116 below an imaginary plane 117 bisecting the sphere at its diameter. The stimulator, truncated at this plane, allows a user more control in effectively concentrating force in the region of the desired acupuncture point L-7 by the application of concentrated or rolling force from the direction of loop fastener section 103 of the wrist band. This might be an appropriate configuration for use during the physical withdrawal from nicotine. Alternatively, a truncation plane 116 chosen closer to 117 will reduce the level of differential stimulation and control when force is applied as described above. This plane might be appropriate for a stimulator employed after physical addiction is quelled.

Stimulator 110 can be of plastic or rubber. Suitable plastics include acrylic or styrene. Suitable rubbers include natural rubber or a synthetic such as butyrate. For rubber stimulators, specifying a shore between 50 and 90 allows a variety of stimulator compliances/resiliences to be prescribed.

It should be noted that while not shown in FIG. 3, a soft rubber stimulator would require a tapped insert at 115 in body 110 to allow screw 111 in FIG. 2 to be used.

In practice a hard plastic stimulator (such as acrylic) could be employed during the early stages of smoking cessation. This would allow more concentrated force to be applied to the region of L-7. During this period a stimulator with a truncation point 116 as indicated in FIG. 3 would further allow the user finer control of acupressure force.

As the length of time from smoking cessation increases, and depending on the smoker's diminishing desire to smoke, increasingly compliant stimulators could be used with the wrist band. These would provide successively lower levels of continuous stimulation to the region of L-7 coupled with successively lower levels of differential stimulation when the wrist band is snapped.

The method by which a user attaches wrist band 100 to his wrist will now be described. While the band can be used on either wrist, for descriptive purposes attachment to the right wrist shall be described.

The user holds wrist band 100 proximal to 110 in his left hand and locates L-7 on his right wrist. Stimulator 110 is lightly pressed into the L-7 hollow and held in place with the thumb of the left hand while the band is simultaneously wrapped around the wrist and secured with fasteners 107 and 108. In the preferred position extensible elastic section 120 is oriented on top of the wrist. The band should be adjusted such that slight pressure is felt in the wrist hollow. The band should not be adjusted so tightly that it interferes with circulation.

FIG. 4 illustrates a perspective view of wrist band 100 attached to a user's right wrist 400 and stretched in region 120 by the thumb and index finger of the user's left hand 410 into stretched state prior to release. The position 415 of acupressure stimulator 110 is located above L-7 acupuncture point 405. In this stretched state stimulator 110 exerts a differential pressure on the region of L-7 relative to the band's pre-stretched state. This has an efficacious effect on L-7 stimulation.

As has been described earlier, the wrist band according to this invention limits the energy that the user can transfer to a unit area of skin, thus limiting what has been called the "sting potential" of the band. By limiting the "sting potential" of the band, development of user aversion to the device is minimized.

In using the wrist band according to this invention, the user stretches wrist band 100 in region 120, as shown in FIG. 4, each time the desire to smoke arises. The band is then released, whereby it snaps against the wrist. The act of snapping the band should be accompanied with positive awareness of the context in which the cigarette was desired, coupled with a user-specific mental image of being "smoke-free". This mental image can either be positive or negative.

On one level, the act of snapping the wrist band acts as a simple replacement for the act of smoking. On another level, the recovering smoker—over time—replaces the desire to smoke with the associations made during the process of snapping the band. On a further level, the band helps the smoker confront the psychological and habituation dimensions of his addiction each time the desire to smoke arises. The wrist band of this invention thereby aids the committed recovering smoker in modifying his behavior.

As stated earlier, differential stimulation of L-7 occurs each time the band is snapped, thus providing therapeutic value in addition to the band's behavioral modification benefits. To heighten such stimulation, especially in the early stage of smoking cessation, it may be advantageous to apply pressure using the thumb of the opposing hand to the region of the stimulator for several seconds immediately after the band is snapped.

When the desire to smoke arises in situations where the act of snapping the wrist band may be socially obtrusive, the user may alternatively apply constant or rotational force to the wrist band proximal to the stimulator. This should be accompanied with the user imagining that he is snapping the wrist band together with enacting the mental imagery described above.

The wrist band of this invention makes it possible for the recovering smoker to continue behavioral modification together with non-invasive smoking-specific acupressure therapy for several months after the period of physical addiction is passed, thus increasing the potential for permanent cessation of smoking.

Although there has been shown and described hereinabove a specific embodiment of a wrist band in accordance with the invention for the purpose of illustrating the manner in which the invention may be used to advantage, it will be appreciated that the invention is not limited thereto. Accordingly, any and all modifications, variations, or equivalent devices which may occur to those skilled in the art should be considered to be within the scope of the invention as defined in the annexed claims. As one example, by removing acupressure stimulator 110, the wrist band can be used strictly as a behavioral modification device to treat other non-desirable behaviors.

What is claimed is:

1. A device for use by an individual to overcome cigarette smoking addiction, comprising:
    a wrist band having an elastic segment with a maximum elongation not in excess of 100% when the elastic segment is stretched without exceeding its elastic limit, The tensile force required to attain said elongation being not in excess of five pounds;
    a non-elastic hook fastener segment with a plurality of hooks attached to the top side of said hook fastener segment;
    a non-elastic loop fastener segment with a plurality of loops attached to the top side of said loop fastener segment;
    an acupressure stimulator comprising a generally curved surface and a generally flat attachment surface for contacting the surface of the human body in the proximal region of the wrist;
    means for attaching the bottom side of said hook fastener segment to said wrist band adjacent a proximal end of said elastic segment;
    means for attaching the bottom side of said loop fastener segment to said wrist band adjacent the distal end of said elastic segment; and
    means for attaching said acupressure stimulator to one side of said wrist band at a selected one of said non-elastic segments.

2. The device of claim 1 wherein the shape of said stimulator is a truncated ellipsoid.

3. The device of claim 1 wherein the shape of said stimulator is a truncated sphere.

4. The device of claim 1 wherein the material forming said stimulator is a non-resilient and non-compliant media.

5. The device of claim 1 wherein the material forming said stimulator is a resilient and compliant media.

6. The device of claim 1 further including means defining an internally tapped recess to receive an attachment screw.

7. The device of claim 1 further including means defining an internal recess for press-fit-receiving a rivet.

8. The device of claim 1 wherein said elastic segment is comprised of an elastic fabric.

9. The device of claim 1 wherein the wrist band is a composite of a resilient material and a non-resilient material.

10. The device of claim 9 wherein said resilient material is rubber and said non-resilient material is polyester.

11. The device of claim 10 wherein said composite is 69% polyester and 31% rubber.

12. The device of claim 1 wherein said band is between 0.50 and 1.0 inch wide.

13. The device of claim 9 wherein said composite of resilient material and non-resilient material is braided in a plurality of rows parallel to the length of said wrist band.

14. The device of claim 1 wherein said hook and loop fastener segments comprise Velcro materials.

15. A device for use by a person to overcome cigarette smoking addiction comprising:
    a wrist band having an intermediate elastic segment extending between first and second non-elastic end segments, said elastic segment having a maximum elongation not in excess of 100% when the elastic segment is stretched without exceeding its elastic limit the tensile force required to attain said elongation being not in excess of five pounds;
    a pair of mating fastener elements attached respectively to said first and second end segments on opposite surfaces of said wrist band; and
    an acupressure stimulator comprising a generally curved surface and a generally flat attachment surface for contacting the surface of the human body in the vicinity of an inner fold of the wrist; and
    means for attaching said acupressure stimulator to said wrist band at a selected one of said non-elastic end segments on the surface of said wrist band away from said selected end segment.

16. The device of claim 15 wherein said acupressure stimulator is mounted to said wrist band with the generally flat attachment surface adjacent the band and the generally curved surface facing away from the band.

17. The device of claim 16 wherein the shape of said stimulator is a truncated ellipsoid.

18. The device of claim 16 wherein the shape of said acupressure stimulator is a truncated sphere.

19. The device of claim 16 wherein the distance between said generally curved surface and said generally flat attachment surface of the acupressure stimulator is sufficient to produce an indentation in the skin of the user adjacent said stimulator when the wrist band is installed about the wrist of the user.

20. The device of claim 15 wherein the elasticity of said elastic segment is sufficient to produce a snapping sensation to the user's skin when the elastic segment is pulled and released while the wrist band is mounted in place about a user's wrist.

21. A pressure-application device for use in acupressure and behavioral-modification therapy to inhibit the desire to smoke in an addicted cigarette smoker by selectively varying the level of applied pressure between predetermined limits at times selected by the user, the device comprising:

a wrist strap to be worn about a user's wrist in the vicinity of a selected acupuncture point;

an inelastic segment at a first end of said strap;

means for mounting an acupressure stimulator on an inner side of said strap in the vicinity of said inelastic segment;

hook and loop fastening means mounted on said strap for securing the strap in place on a user's wrist; and an elastic segment of said wrist strap connected to said inelastic segment, said elastic segment being fabricated to permit a selectable variation of applied pressure from said acupressure stimulator between predetermined limits in order to restrict the degree of pain to a non-aversive level when said strap is snapped against the wrist, said elastic segment having a maximum elongation not in excess of 100% when stretched without exceeding its elastic limit, the tensile force required to attain said elongation being not in excess of five pounds.

22. A method for using a pressure application device for both acupressure and behavioral modification therapy to aid an addicted cigarette smoker in quitting smoking, which device comprises:

a wrist strap to be worn about a user's wrist in the vicinity of a selected acupuncture point;

an inelastic segment at a first end of said strap;

means for mounting an acupressure stimulator on an inner side of said strap in the vicinity of said inelastic segment;

hook and loop fastening means mounted on said strap for securing the strap in place on a user's wrist; and an elastic segment of said wrist strap connected to said inelastic segment, said elastic segment being fabricated to permit a selectable variation of applied pressure from said acupressure stimulator between predetermined limits in order to restrict the degree of pain to a non-aversive level when said strap is snapped against the wrist;

said method comprising the steps of:
  A. positioning the acupressure stimulator of said device on one of said smoker's arms in close proximity to the Lieque acupuncture point located proximal to the styloid process of the radius bone above the smoker's wrist crease;
  B. wrapping the wrist strap of said device around sad smoker's arm until slight pressure upon said Lieque point is felt by the smoker;
  C. securing said wrist strap on said smoker's arm while maintaining said slight pressure by the hook and loop fastener means of said device;
  D. pulling said wrist strap away from said arm in a direction perpendicular to said radius and opposite to said wrist crease in order to provide differential stimulation to the Lieque acupuncture point each time the desire to smoke arises; and
  E. releasing said wrist strap to cause a slight, non-aversive stinging sensation when said wrist strap contacts said arm as a behavioral modification strategy.

23. The method of claim 22 further including the steps of:

substituting a more compliant acupressure stimulator for the acupressure stimulator of said device; and repeating steps A through E.

24. The method of claim 22 wherein the acupressure stimulator of said device is formed of hard plastic material and further comprising the steps of sequentially replacing the stimulator with increasingly more compliant stimulators and after each stimulator replacement repeatedly performing the series of steps A through E until the smoker's desire to smoke decreases.

25. The method of claim 22 further including the step of manually applying pressure to the acupressure stimulator for a period of several seconds immediately after performing steps D and E.

26. The method of claim 22 comprising the step of manually applying pressure to the acupressure stimulator for a period of several seconds instead of performing steps D and E.

* * * * *